US00PP26017P3

(12) United States Plant Patent
Olesen

(10) Patent No.: US PP26,017 P3
(45) Date of Patent: Oct. 27, 2015

(54) MINIATURE ROSE PLANT NAMED 'POULTY015'

(50) Latin Name: ***Rosa* hybrid**
Varietal Denomination: Poulty015

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 168 days.

(21) Appl. No.: 13/986,938

(22) Filed: Jun. 14, 2013

(65) Prior Publication Data

US 2014/0373208 P1 Dec. 18, 2014

(51) Int. Cl.
*A01H 5/02* (2006.01)

(52) U.S. Cl.
USPC ..... Plt./118

(58) Field of Classification Search
USPC ..... Plt./118, 120, 125, 127
CPC ..... A01H 5/0222; A01H 5/0216; A01H 5/02; A01H 5/00
See application file for complete search history.

(56) References Cited

PUBLICATIONS

Help Me Find Dec Rose, retrieved on Jan. 14, 2015, retrieved from the Internet at <retrieved from the Internet at <www.helpmefind.com/gardening/l.php?l=2.71252> one page.*

Upov Pluto Plant Variety Database 20150114, retrieved on Jan. 14, 2015, retrieved from the Internet <www3.wipo.int/pluto/user/en/index.jsp> for Rosa Poulty015 one page.*

* cited by examiner

*Primary Examiner* — June Hwu

(57) ABSTRACT

A new miniature rose plant that has abundant, golden yellow flowers and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical designation: *Rosa* hybrid.
Variety denomination: 'Poulty015'.

SUMMARY OF THE INVENTION

The present invention constitutes a new and distinct variety of miniature rose plant which originated from a controlled crossing between the female seed parent, an unnamed seedling, and the male pollen parent, also an unnamed seedling.

The two parents were crossed during the summer of 2007 and the resulting seeds were planted in a controlled environment in Fredensborg, Denmark. The new variety, named 'Poulty015', originated as a single seedling from the stated cross.

The new variety may be distinguished from its male pollen parent and female seed parent primarily by flower coloration and growth habit.

The objective of the hybridization of this rose variety for commercial culture was to create a new and distinct variety with unique qualities, such as:

1. Uniform and abundant golden yellow flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventor, and distinguish 'Poulty015' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulty015' was selected by the inventor as a single plant from the progeny of the hybridization in 2007.

Asexual reproduction of 'Poulty015' by vegetative stem cuttings was first done by Mogens N. Olesen in the nursery in Fredensborg, Denmark in 2008. This initial and other subsequent propagations conducted in controlled environments have demonstrated that the characteristics of 'Poulty015' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulty015'. Specifically illustrated in the drawing are flowers at various stages of development, flower in parts, leaves, and stems.

DETAILED DESCRIPTION OF THE VARIETY

The following is a description of 'Poulty015', as observed in its growth in glasshouses in Half Moon Bay, Calif. Observed plants are 3 months of age and were cultivated in 10.5 cm pots. Color references are made using The Royal Horticultural Society (London, England) Colour Chart, 2001, except where common terms of color are used.

For a comparison, several physical characteristics of the rose variety 'Poulmist', U.S. Plant Pat. No. 18,975 are compared to 'Poulty015' in Chart 1.

CHART 1

| | 'Poulty015' | 'Poulmist' |
|---|---|---|
| Petalage: | 75 petals total, 20 to 25 of which are petaloids | 35 to 40 petals |
| Flower Diameter: | 50 mm | 40 mm |
| General Tonality of Flower Color: | On open flower Yellow Group 10C with intonations of Yellow-Orange Group 23C | Yellow Group 12B |

FLOWER AND FLOWER BUD

Blooming habit: Continuous.

Flower bud:

*Size.*—Upon opening, 21 mm in length from base of receptacle to end of bud. 19 mm in diameter.

*Bud form.*—Ovate.

*Bud color.*—As sepals unfold, petals are Orange Group 29C, Yellow-Orange Group 18B, and Yellow Group 8C.

*Sepals.*—Upper Surface: Color: Yellow-Green Group 144B. Texture: Smooth, moderately pubescent. Lower Surface: Color: Yellow Green Group 144A. Texture: Smooth. Shape: Apex: Cirrhose. Base: Flat at union with receptacle. Margins: Margins have moderate foliaceous appendages on three of the five sepals. Size: 25 mm long by 7 mm wide.

*Receptacle.*—Surface Texture: Smooth. Shape: Broad funnel shaped. Size: 5 mm tall and 9 mm wide. Color: Yellow Green Group 144B.

*Pedicel.*—Surface: Somewhat rough due to the presence of stipitate glands. Length: 20 mm on average. Diameter: Generally 3 mm. Color: Yellow-Green Group 145B. Strength: Strong.

*Borne.*—Singly.

Flower bloom:

*Fragrance.*—Moderate floral scent.

*Duration.*—As a pot plant, flowers last up to 28 days.

*Size.*—Flower diameter is 50 mm when open. Flower depth is 25 mm.

*Form.*—General shape is a hybrid tea with a high pointed center. As the flower opens, the central whorl of petals divides into quarter sections.

*Shape of flower, side view.*—Upon opening, the upper portion is flat. The lower portion is concave.

Petalage: Double. Under normal conditions, flowers have 75 petals total, 20 to 25 of which are petaloids.

Color:

*General tonality.*—On open flower Yellow Group 10C with intonations of Yellow-Orange Group 23C.

*Petals.*—Outermost petals are Yellow Group 8C with light shaded intonations of Yellow-Orange Group 18B on the upper surface. Lower surface is Yellow Group 8B with shaded intonations of Orange Group 26B. Innermost petals are Yellow Group 8C with light shaded intonations of Yellow-Orange Group 18B on the upper surface. Lower surface is Yellow Group 8B with shaded intonations of Orange Group 26B to Red Group 40D. No basal petal spots. The petal color is the same for flowers upon opening and after opening.

Petal characteristics:

*Petal reflex.*—Strong and moderate.

*Margin.*—Entire, with a slight point at the center, slight undulations.

*Shape.*—Overall, broad elliptic. Apex shape: Cuspidate. Base shape: Obtuse.

*Size.*—26 mm (l) by 30 mm (w).

*Texture.*—Smooth.

*Thickness.*—Average.

Petaloids:

*Quantity.*—20 to 25 on average.

*Shape.*—Rounded. The apex is rounded. The base is acute.

*Color.*—Upper and lower surfaces are Yellow Group 8C with intonations of Red Group 48C at margins.

*Size:* 6 mm (l) by 6 mm (w).

Reproductive organs:

*Pollen.*—None Observed.

*Anthers.*—Size: 1 mm long. Color: Yellow Group 9B. Quantity: 10 on average.

*Filaments.*—Color: Green-White Group 157C. Length: About 1 mm.

*Pistils.*—Length: About 3 mm long. Quantity: 10 on average.

*Stigmas.*—Superior relative to the length of the filaments and the height of the anthers. Color: Yellow Group 1D.

*Styles.*—Color: Yellow Group 1D.

*Seed formation.*—Not observed.

PLANT

Plant growth: Upright. Plants are 16 cm in height on average, and 13 cm wide.

Stems:

*Color.*—Juvenile growth: Yellow-Green Group 144B. Mature growth: Yellow-Green Group 144A.

*Length.*—Canes are 10 cm from the base of the plant to the flowering portion.

*Diameter.*—3 mm.

*Internodes.*—On mature canes, there is an average distance of 21 mm between nodes.

*Surface texture.*—Young and mature wood is smooth.

Prickles: None observed.

Plant foliage:

*Compound leaf size.*—80 mm (l) by 45 mm (w).

*Quantity.*—5 leaves per 10 cm of stem.

*Leaf bearing angle.*—60 degrees to the stem.

*Color of juvenile foliage.*—Upper Leaf Surface: Yellow-Green Group 144A with anthocyanin the color of Greyed-Purple Group 184A. Lower Leaf Surface: Yellow-Green Group 144A with anthocyanin the color of Greyed-Purple Group 184A.

*Color of mature foliage.*—Upper Leaf Surface: Yellow-Green Group 147A. Lower Leaf Surface: Yellow-Green Group 147B.

Plant leaves and leaflets:

*Stipules.*—Size: About 4 mm in length. Shape: Linear, slightly broad based with outward extending apecies. Margins: Finely serrated with few stipitate glands. Color: Yellow-Green Group 144A.

*Petiole*.—Length: 12 mm on average. Diameter: About 1 mm. Upper surface: Yellow-Green Group 146B. Stipitate glands. Lower surface: Yellow-Green Group 144B. Small prickles.

*Disease resistance*.—Average resistance to powdery mildew *Sphaerotheca pannosa*, downy mildew *Peronospora sparsa*, rust *Phragmidium sps.*, black spot *Diplocarpon rosae*, and *Botrytis cinerea* under normal growing conditions.

*Rachis*.—Length: 30 mm on average. Diameter: About 1 mm. Upper surface: Yellow-Green Group 146B. Stipitate glands. Lower surface: Yellow-Green Group 144B. Small prickles.

*Leaflet*.—Number of leaflets: 5 on normal leaves in middle of the stem. Occasionally 7 leaflets. Size: 34 mm in length by 21 mm wide. Margin: Serrate. General Shape: Elliptical. Apex Shape: Acute. Base Shape: Round. Texture: Smooth. Arrangement: Odd pinnate. Venation: Reticulate. Leaf Gloss: Slightly glossy.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the miniature class named 'Poulty015', substantially as illustrated and described herein, due to its abundant, golden yellow flowers, vigorous growth, compact habit, suitability for production from softwood cuttings in pots, and durable flowers and foliage that make the variety suitable for distribution in the floral industry.

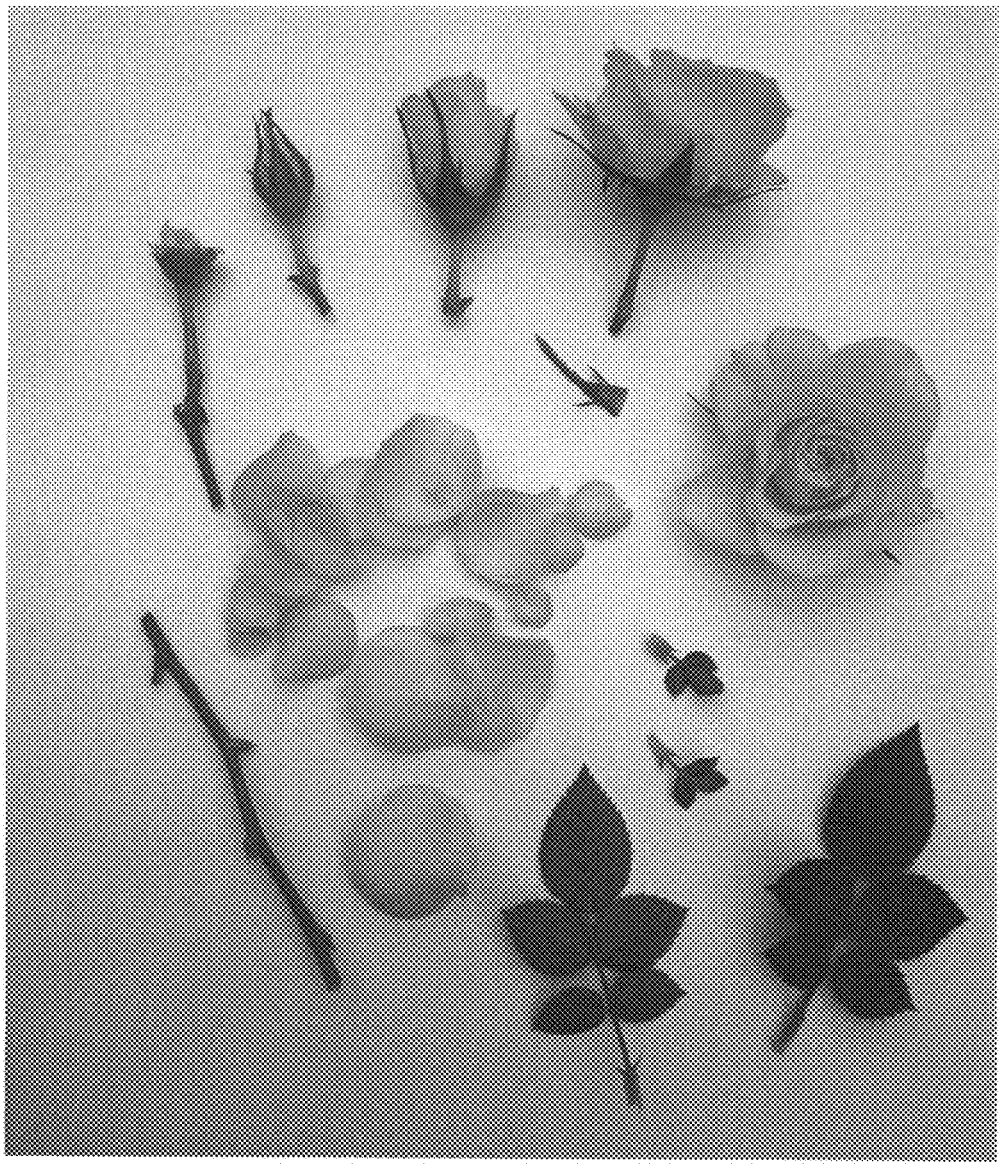

* * * * *